US012658282B2

(12) United States Patent
Kasahara

(10) Patent No.: US 12,658,282 B2
(45) Date of Patent: Jun. 16, 2026

(54) METHOD FOR GENERATING IMAGE PROCESSING SEQUENCE, GENERATION DEVICE, AND NON-TRANSITORY COMPUTER-READABLE STORAGE MEDIUM STORING COMPUTER PROGRAM

(71) Applicant: SEIKO EPSON CORPORATION, Tokyo (JP)

(72) Inventor: Hideaki Kasahara, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 389 days.

(21) Appl. No.: 18/359,921

(22) Filed: Jul. 27, 2023

(65) Prior Publication Data

US 2024/0038334 A1     Feb. 1, 2024

(30) Foreign Application Priority Data

Jul. 27, 2022     (JP) ................................ 2022-119709

(51) Int. Cl.
| | |
|---|---|
| *G06V 10/776* | (2022.01) |
| *G06V 10/75* | (2022.01) |
| *G06V 10/771* | (2022.01) |
| *G16B 30/00* | (2019.01) |

(52) U.S. Cl.
CPC ........... *G16B 30/00* (2019.02); *G06V 10/751* (2022.01); *G06V 10/771* (2022.01); *G06V 10/776* (2022.01)

(58) Field of Classification Search
CPC ...... G16B 30/00; G16B 40/20; G06V 10/751; G06V 10/771; G06V 10/776; G06V 10/764; G06V 10/774; G06V 10/82
See application file for complete search history.

(56) References Cited

U.S. PATENT DOCUMENTS

| | | | | |
|---|---|---|---|---|
| 2020/0082913 A1* | 3/2020 | Mir | ........................... | G06N 7/01 |
| 2021/0042550 A1* | 2/2021 | Nagato | ................ | G06V 10/762 |
| 2021/0279866 A1* | 9/2021 | Svekolkin | ................. | G06T 7/11 |
| 2022/0229862 A1* | 7/2022 | Kappel | ................. | G16H 30/20 |
| 2023/0316707 A1* | 10/2023 | Kanai | ................... | G06T 7/0004 |
| | | | | 382/218 |

FOREIGN PATENT DOCUMENTS

| | | | |
|---|---|---|---|
| JP | 2006337152 A | | 12/2006 |
| JP | 2007087055 A | | 4/2007 |
| JP | 2017162069 A | * | 9/2017 |

* cited by examiner

*Primary Examiner* — Kathleen M Broughton
(74) *Attorney, Agent, or Firm* — CHIP LAW GROUP

(57) ABSTRACT

In a method for generating an image processing sequence, when selecting a learning set, a probability of selection of the learning set having a predetermined value, of a plurality of subject evaluation values corresponding respectively to two or more learning sets calculated in a previous routine, is increased.

8 Claims, 9 Drawing Sheets

70

STORAGE DEVICE

| | |
|---|---|
| 74 LEARNING DATA | 89 SELECTION TABLE |
| 80 IMAGE FILTER GROUP | DSq SPECIFIED IMAGE PROCESSING SEQUENCE |
| 82 GENE TABLE | 94 VARIOUS PROGRAMS |
| 84 POPULATION | |

SM,74

DA

DA

LM

TM

TID=T01

| FILTER TYPE | NUMBER OF IN-PUTS | NUMBER OF OUT-PUTS | RANGE OF APPEARANCE |
|---|---|---|---|
| FtA | 1 | 1 | $0 \leq VG < 0.167$ |
| FtB | 1 | 1 | $0.167 \leq VG < 0.333$ |
| FtC | 1 | 1 | $0.333 \leq VG < 0.500$ |
| FtD | 2 | 1 | $0.500 \leq VG < 0.667$ |
| FtE | 2 | 1 | $0.667 \leq VG < 0.833$ |
| in | 0 | 1 | $0.833 \leq VG \leq 1.000$ |

START

S10
GENERATION PROCESSING FOR SPECI-
FIED IMAGE PROCESSING SEQUENCE

S50
USE PROCESSING PROCESS USING SPECI-
FIED IMAGE PROCESSING SEQUENCE

END

FIG. 8

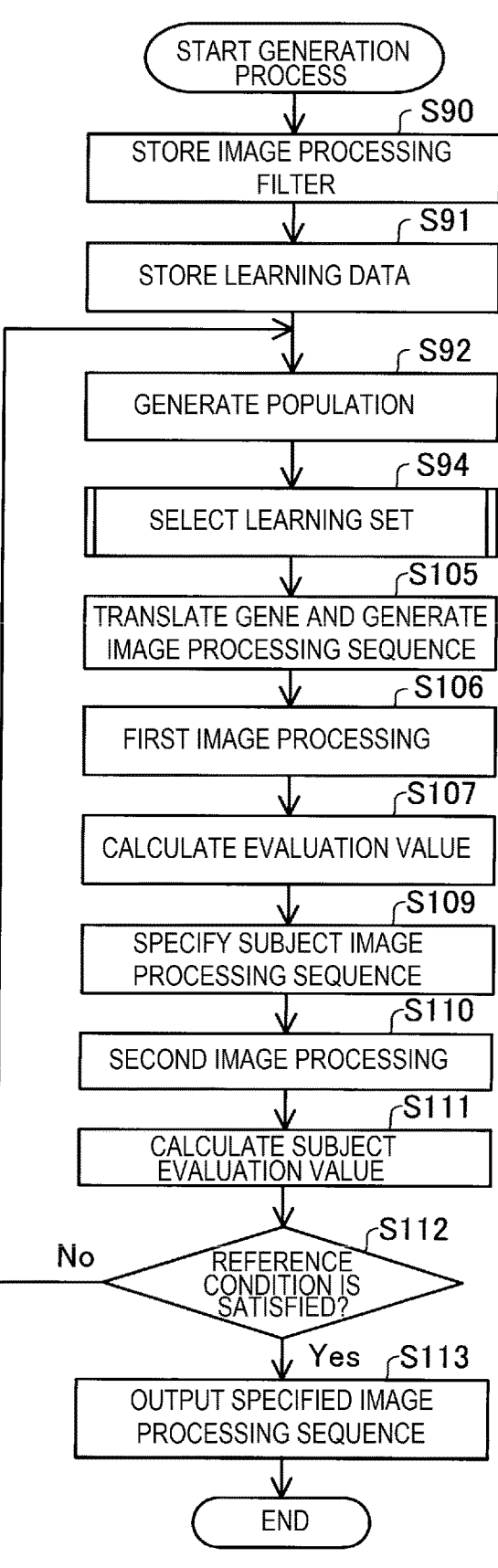

START GENERATION PROCESS

S90
STORE IMAGE PROCESSING FILTER

S91
STORE LEARNING DATA

S92
GENERATE POPULATION

S94
SELECT LEARNING SET

S105
TRANSLATE GENE AND GENERATE IMAGE PROCESSING SEQUENCE

S106
FIRST IMAGE PROCESSING

S107
CALCULATE EVALUATION VALUE

S109
SPECIFY SUBJECT IMAGE PROCESSING SEQUENCE

S110
SECOND IMAGE PROCESSING

S111
CALCULATE SUBJECT EVALUATION VALUE

S112
REFERENCE CONDITION IS SATISFIED?    No

Yes    S113
OUTPUT SPECIFIED IMAGE PROCESSING SEQUENCE

END

FIG. 9

CURRENT GENERATION Gm

| INDIVIDUAL ID | T01 | T02 | T03 | T04 | T05 | T06 | T07 | T08 | EVALUATION VALUE OF LEARNING SET FEV | STATISTIC OF SUBJECT EVALUATION VALUE (AVERAGE VALUE) |
|---|---|---|---|---|---|---|---|---|---|---|
| I001 | 0.554 | 0.473 | 0.470 | 0.729 | 0.133 | 0.838 | 0.537 | 0.200 | 0.632 | 0.500 |
| I002 | | 0.881 | | 0.161 | | | | | 0.521 | |
| I003 | | 0.623 | | 0.287 | | | | | 0.455 | |
| I004 | | 0.174 | | 0.506 | | | | | 0.340 | |
| I005 | | 0.202 | | 0.694 | | | | | 0.448 | |
| I006 | | 0.890 | | 0.031 | | | | | 0.461 | |
| I007 | | 0.119 | | 0.128 | | | | | 0.123 | |
| I008 | | 0.692 | | 0.275 | | | | | 0.484 | |
| I009 | | 0.232 | | 0.041 | | | | | 0.136 | |
| I010 | | 0.843 | | 0.030 | | | | | 0.436 | |

LEARNING SET TID

NEXT GENERATION Gn

| INDIVIDUAL ID | LEARNING SET TID | | | | | | | | EVALUATION VALUE OF LEARNING SET FEV | STATISTIC OF SUBJECT EVALUATION VALUE (AVERAGE VALUE) |
|---|---|---|---|---|---|---|---|---|---|---|
| | T01 | T02 | T03 | T04 | T05 | T06 | T07 | T08 | | |
| I001 | 0.554 | 0.473 | 0.470 | 0.729 | 0.133 | 0.838 | 0.537 | 0.200 | 0.632 | 0.500 |
| I002 | | 0.881 | 0.977 | 0.161 | | | | 0.723 | 0.521 | |
| I003 | | 0.623 | | 0.287 | | | | | 0.455 | |
| I004 | | 0.174 | 0.032 | 0.506 | | | | 0.257 | 0.340 | |
| I005 | | 0.202 | | 0.694 | | | | | 0.418 | |
| I006 | | 0.890 | | 0.031 | | | | | 0.461 | |
| I007 | | 0.119 | | 0.128 | | | | | 0.123 | |
| I008 | 0.382 | 0.692 | 0.784 | 0.275 | 0.098 | 0.836 | 0.057 | 0.917 | 0.851 | 0.505 |
| I009 | | 0.232 | | 0.041 | | | | 0.136 | 0.136 | |
| I010 | | 0.843 | | 0.030 | | | | 0.436 | 0.436 | |
| I011 | | | 0.556 | | | | | 0.085 | 0.320 | |
| I012 | | | 0.308 | | | | | 0.745 | 0.526 | |
| I013 | | | 0.930 | | | | | 0.439 | 0.685 | |
| I014 | | | 0.872 | | | | | 0.343 | 0.608 | |
| I015 | | | 0.248 | | | | | 0.712 | 0.480 | |
| I016 | | | 0.142 | | | | | 0.917 | 0.529 | |

S94   S112   S109   S107   S111

| IDENTIFICATION NUMBER OF LEARNING SET | SELECTION RANGE |
|---|---|
| T01 | $0 \leq SR < 0.125$ |
| T02 | $0.125 \leq SR < 0.250$ |
| T03 | $0.250 \leq SR < 0.375$ |
| T04 | $0.375 \leq SR < 0.500$ |
| T05 | $0.500 \leq SR < 0.625$ |
| T06 | $0.625 \leq SR < 0.750$ |
| T07 | $0.750 \leq SR < 0.875$ |
| T08 | $0.875 \leq SR \leq 1.000$ |

FIG. 13

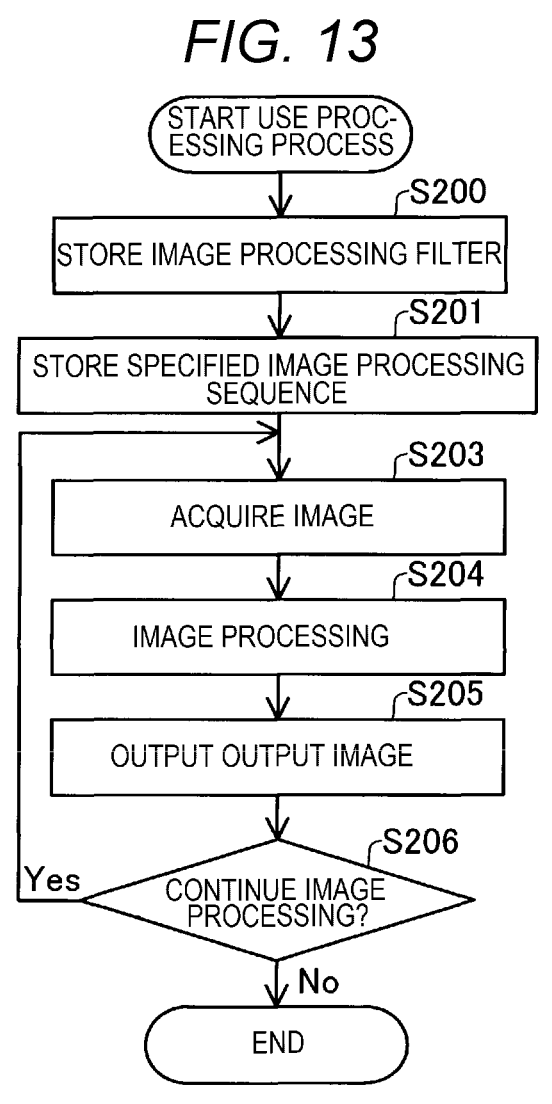

START USE PROC-
ESSING PROCESS

↓ S200

STORE IMAGE PROCESSING FILTER

↓ S201

STORE SPECIFIED IMAGE PROCESSING
SEQUENCE

↓ S203

ACQUIRE IMAGE

↓ S204

IMAGE PROCESSING

↓ S205

OUTPUT OUTPUT IMAGE

↓ S206

CONTINUE IMAGE
PROCESSING?

Yes

↓ No

END

METHOD FOR GENERATING IMAGE PROCESSING SEQUENCE, GENERATION DEVICE, AND NON-TRANSITORY COMPUTER-READABLE STORAGE MEDIUM STORING COMPUTER PROGRAM

The present application is based on, and claims priority from JP Application Serial Number 2022-119709, filed Jul. 27, 2022, the disclosure of which is hereby incorporated by reference herein in its entirety.

BACKGROUND

1. Technical Field

The present disclosure relates to a technique for generating an image processing sequence.

2. Related Art

According to the related art, a technique of expressing an individual structurally like a tree structure, using genetic programming, is known. JP-A-2007-87055 is an example of this technique. Also, according to the related art, a technique of calculating a feature value of an inspection area image having a defect in an inspection area in relation to a teaching image having an inspection area, and changing the calculated feature value to generate a changed inspection area image, is known. JP-A-2006-337152 is an example of this technique.

In the technique of JP-A-2007-87055, an image processing sequence formed of a plurality of image processing filters combined together in a tree structure is generated by using genetic programming. Then, a result image formed by image-processing a learning image according to the image processing sequence and a target image are compared with each other, and a plurality of current-generation image processing sequences are thus evaluated. A high-rated image processing sequence is maintained also in the next generation. Meanwhile, for a low-rated image processing sequence, a new image processing sequence is generated, using a technique such as crossover or mutation. Then, a next-generation image processing sequence set is generated, using the image processing sequence maintained in the current generation and the newly generated image processing sequence. The generation and the evaluation of an image processing sequence set are repeated until a desired image processing sequence is acquired. In the technique of JP-A-2007-87055, if the number of learning images used for the evaluation is increased in order to restrain overlearning, the number of times of the image processing according to an image processing sequence and the number of times of the evaluation increase. Therefore, in the technique of JP-A-2007-87055, a long processing time may be taken until a desired image processing sequence is acquired.

In the technique of JP-A-2006-337152, a generated changed inspection area image is arranged on the same one image as an inspection area image. However, the number and types of inspection area images that can be arranged on one image are limited. In the technique of JP-A-2006-337152, the feature value of an inspection area image having a defect is changed to generate a new changed inspection area image. Therefore, this technique cannot be applied when preparing a plurality of types of good-quality images without any defect. Thus, a long processing time may be taken to prepare a plurality of types of good-quality images without any defect and perform an evaluation using an image processing sequence in order to improve the evaluation accuracy.

As described above, according to the related art, a technique that can reduce the processing time to acquire a desired image processing sequence is demanded.

SUMMARY

According to a first aspect of the present disclosure, a method for generating an image processing sequence is provided. The method for generating the image processing sequence includes: (a) preparing a plurality of learning sets, the learning set including a learning image and a target image associated with the learning image; (b) generating a sequence set formed of a plurality of image processing sequences, the image processing sequence representing a combination of (i) an image input layer to input an image, (ii) at least one of a plurality of image processing layers, and (iii) an image output layer to output the image after image processing, as sequence elements, the combination varying between the plurality of the image processing sequences; (c) selecting a smaller number of the learning sets than the plurality of the learning sets, from among the plurality of the learning sets; (d) image-processing the learning image in the learning set selected in the (c), according to each of the plurality of the image processing sequences, and generating an output image that is an image after the image processing for each of the plurality of the image processing sequences; (e) comparing the output image and the target image associated with the learning image serving as a base of the output image, and calculating an evaluation value indicating a degree of similarity between the output image and the target image, for each of the plurality of the image processing sequences; (f) specifying a subject image processing sequence that is the image processing sequence where the degree of similarity is the highest, of a plurality of the evaluation values corresponding respectively to the plurality of the image processing sequences; (g) image-processing the learning image of each of the learning sets that are more than the number of the learning sets selected in the (c), of the plurality of the learning sets, and that are two sets or more including the learning set selected in the (c), according to the subject image processing sequence, thus generating the output image, comparing the output image and the target image associated with the learning image serving as the base of the output image, and calculating a subject evaluation value as the evaluation value; and (h) determining whether the subject image processing sequence satisfies a predetermined reference condition or not, using the subject evaluation value. The method for generating the image processing sequence repeatedly executes the (b) to the (h) until the subject image processing sequence satisfies the reference condition. When selecting the learning set in the (c), a probability of selection of the learning set having a predetermined value, of a plurality of the subject evaluation values corresponding respectively to the two sets or more of the learning sets calculated in the (g) in a previous routine, is increased.

According to a second aspect of the present disclosure, a generation device for an image processing sequence is provided. The generation device includes: a sequence generation unit generating a sequence set formed of a plurality of image processing sequences, the image processing sequence representing a combination of (i) an image input layer to input an image, (ii) at least one of a plurality of image processing layers, and (iii) an image output layer to output the image after image processing, as sequence elements, the combination varying between the plurality of the image processing sequences; a selection unit selecting, from among a plurality of learning sets where the learning set is a combination of a learning image prepared in advance and a target image, a smaller number of the learning sets than the plurality of the learning sets; an image processing unit image-processing the learning image in the learning set selected by the selection unit, according to each of the plurality of the image processing sequences, and generating an output image that is an image after the image processing for each of the plurality of the image processing sequences; a calculation unit comparing the output image and the target image forming the learning set with the learning image serving as a base of the output image, and calculating an evaluation value indicating a degree of similarity between the output image and the target image, for each of the plurality of the image processing sequences; and a specification unit specifying a subject image processing sequence that is the image processing sequence where the degree of similarity is the highest, of a plurality of the evaluation values corresponding respectively to the plurality of the image processing sequences. The image processing unit image-processes the learning image of each of the learning sets that are more than the number of the learning sets selected by the selection unit, of the plurality of the learning sets, and that are two sets or more including the learning set selected by the selection unit, according to the subject image processing sequence, and thus generates a subject output image as the output image. The calculation unit compares the subject output image and the target image associated with the learning image serving as the base of the subject output image, and calculates a subject evaluation value as the evaluation value. The specification unit determines whether the subject image processing sequence satisfies a predetermined reference condition or not, using the subject evaluation value. When the subject image processing sequence does not satisfy the reference condition, the selection unit increases a rate of selection of the learning set having a predetermined value, of a plurality of the subject evaluation values corresponding respectively to the two sets or more of the learning sets calculated by the calculation unit, and newly selects the learning set, and the sequence generation unit generates the sequence set that is for the newly selected learning set and that differs from the sequence set which is generated previously.

According to a third aspect of the present disclosure, a non-transitory computer-readable storage medium storing a computer program is provided. The computer program causes a computer to execute: (a) a sequence generation function of generating a sequence set formed of a plurality of image processing sequences, the image processing sequence representing a combination of (i) an image input layer to input an image, (ii) at least one of a plurality of image processing layers, and (iii) an image output layer to output the image after image processing, as sequence elements, the combination varying between the plurality of the image processing sequences; (b) a function of selecting, from among a plurality of learning sets where the learning set is a combination of a learning image prepared in advance and a target image associated with the learning image, a smaller number of the learning sets than the plurality of the learning sets; (c) a function of image-processing the learning image in the learning set selected by the function (b), according to each of the plurality of the image processing sequences, and generating an output image that is an image after the image processing for each of the plurality of the image processing sequences; (d) a function of comparing the output image and the target image associated with the learning image serving as a base of the output image, and calculating an evaluation value indicating a degree of similarity between the output image and the target image, for each of the plurality of the image processing sequences; (e) a function of specifying a subject image processing sequence that is the image processing sequence where the degree of similarity is the highest, of a plurality of the evaluation values corresponding respectively to the plurality of the image processing sequences; (f) a function of image-processing the learning image of each of the learning sets that are more than the number of the learning sets selected by the function (b), of the plurality of the learning sets, and that are two sets or more including the learning set selected by the function (b), according to the subject image processing sequence, thus generating the output image, comparing the output image and the target image associated with the learning image serving as the base of the output image, and calculating a subject evaluation value as the evaluation value; and (g) a function of determining whether the subject image processing sequence satisfies a predetermined reference condition or not, using the subject evaluation value. The computer program causes the computer to repeatedly execute the function (a) to the function (g) until the subject image processing sequence satisfies the reference condition. The function (b) has a function of increasing a probability of selection of the learning set having a predetermined value, of a plurality of the subject evaluation values corresponding respectively to the two sets or more of the learning sets calculated by the function (f) in a previous routine, when selecting the learning set.

BRIEF DESCRIPTION OF THE DRAWINGS

FIG. 8 is a flowchart showing details of a generation process of step S10.

FIG. 9 is a first chart for explaining the generation process of step S10.

FIG. 10 is a second chart for explaining the generation process of step S10.

FIG. 13 is a flowchart showing a use processing process.

DESCRIPTION OF EXEMPLARY EMBODIMENTS

A. Embodiment

Figure 1:
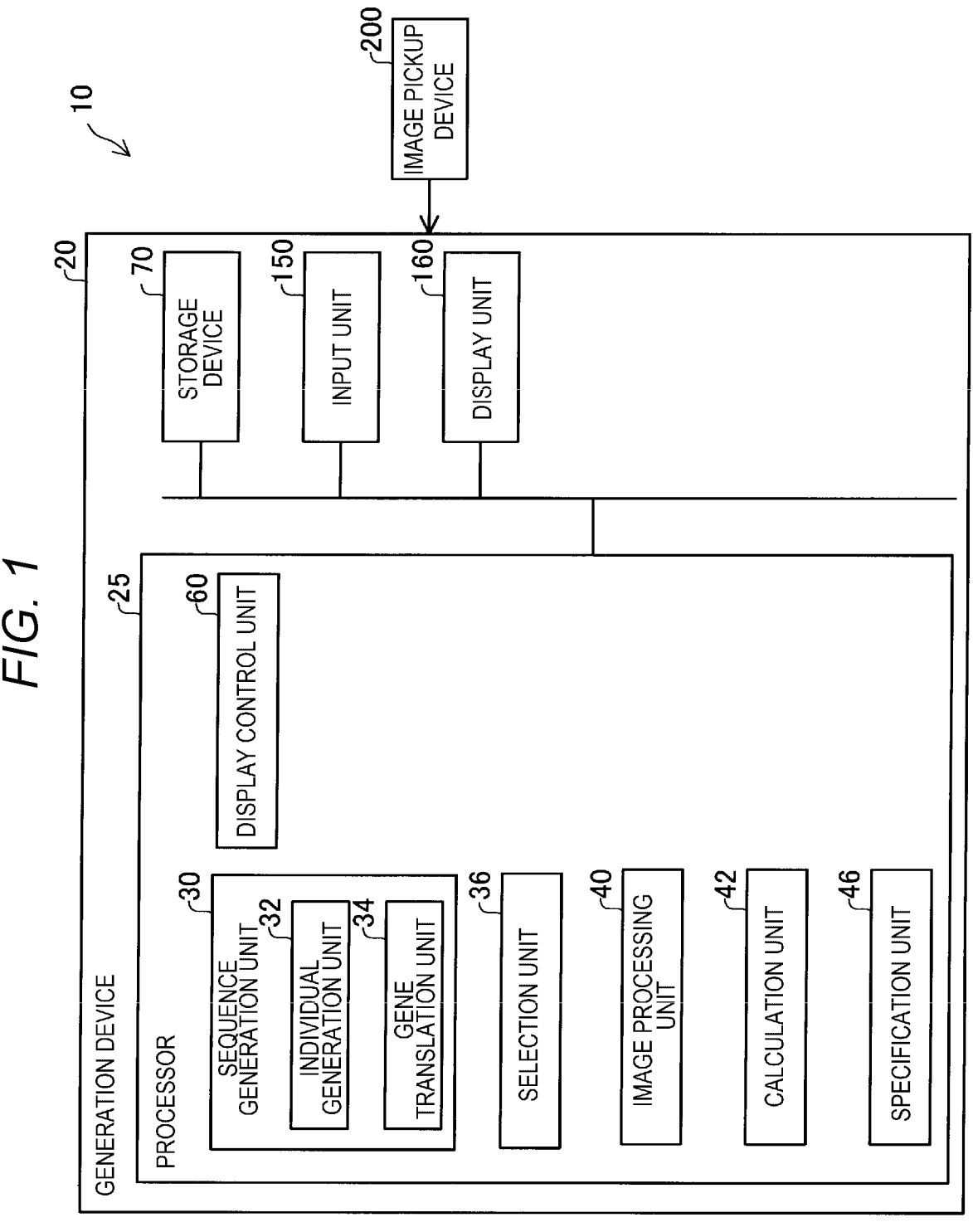
FIG. 1 explains a generation system according to an embodiment.

FIG. 1 explains a generation system 10 according to an embodiment. The generation system 10 has a generation device 20 and an image pickup device 200. The generation device 20 and the image pickup device 200 can transmit and receive data to and from each other via a wire or wirelessly. The image pickup device 200 is a camera. The image pickup device 200 picks up an image of a subject and acquires a picked-up image. The picked-up image acquired by the image pickup device 200 is transmitted to the generation device 20.

The generation device 20 has a sequence generation function of generating a specified image processing sequence DSq for acquiring a desired image after image processing, and an image processing function of image-processing an image according to the specified image processing sequence DSq generated by the sequence generation function, and thus outputting a processed image. The generation device 20 in this embodiment automatically generates the specified image processing sequence DSq for acquiring an image to achieve a desired objective, based on the picked-up image. For example, the generation device 20 image-processes an image of a circuit board, which is an industrial product, picked up by the image pickup device 200, using the specified image processing sequence DSq, and thus outputs a binarized image where a defect part is expressed as a black image whereas the other parts are expressed as a white image, as the processed image. Based on the binarized image, a user or a device specifies whether there is a defect part or not, and the location of a defect part if any. An inspection of the industrial product is thus carried out.

The sequence generation function generates a plurality of image processing sequences Sq, using genetic programming. The sequence generation function also specifies the specified image processing sequence DSq for acquiring a desired image after image processing, from among the plurality of image processing sequences Sq thus generated. In this embodiment, the sequence generation function and the image processing function are installed in one generation device 20. However, this is not limiting. In another embodiment, the sequence generation function and the image processing function may be installed in separate devices or may be present on a cloud.

The generation device 20 is an electronic computer such as a personal computer. The generation device 20 has a processor 25, a storage device 70, an input unit 150, and a display unit 160. The processor 25 executes various programs stored in the storage device 70 and thus controls operations of the generation device 20. Detailed functions of the processor 25 will be described later. The storage device 70 is formed of a memory such as a RAM or a ROM. The storage device 70 stores various programs for implementing each function of the processor 25, and various data used to generate the image processing sequence Sq. Details of the storage device 70 will be described later. The input unit 150 is an interface accepting information from outside. For example, the input unit 150 accepts an input of a picked-up image from the image pickup device 200 and accepts an input of an image generated by the user using another device. The display unit 160 displays various information. The display unit 160 is, for example, a liquid crystal monitor.

The processor 25 executes various programs in the storage device 70 and thus functions as a sequence generation unit 30, a selection unit 36, an image processing unit 40, a calculation unit 42, a specification unit 46, and a display control unit 60. A part of the functions executed by the processor 25 may be implemented by a hardware circuit. In the present disclosure, the "processor" is a term including CPU and GPU.

The sequence generation unit 30 generates a sequence set formed of a plurality of image processing sequences Sq having different combinations of sequence elements from each other, by structurally expressing a gene sequence represented by an individual IV like a tree structure. The image processing sequence Sq is expressed by a combination of a plurality of sequence elements. The sequence elements include (i) an image input layer, which is a node to input an image, (ii) an image processing layer as an image processing filter, which is an intermediate node between the image input layer and an image output layer, and (iii) the image output layer, which is a node to output an output image PM, which is an image after image processing, that is, after final image processing.

The sequence generation unit 30 has an individual generation unit 32 and a gene translation unit 34. The individual generation unit 32 generates an individual IV formed of a plurality of genes sequenced one-dimensionally or two-dimensionally. The genes forming the individual IV are numerical values indicating the image input layer and the type of the image processing layer, and in this embodiment, the image processing filter. The image input layer and a different image processing filter are allocated to each numerical range. That is, the individual IV is generated by sequencing genes corresponding to the image input layer and the image processing layer, respectively. The individual generation unit 32 generates a predetermined number of individuals IV for each generation G. In this embodiment, the individual generation unit 32 sequences genes one-dimensionally and thus generates an individual IV having a predetermined gene length. The combination of sequence elements of a plurality of image processing sequences Sq varies from one generation G to another. For a first generation, which is the very first generation, the individual generation unit 32 randomly arranges numerical values down to the third decimal place from 0 to 1 as genes in loci of an individual IV, and thus generates a population 84 formed of a plurality of individuals IV. From the second generation onward, the individual generation unit 32 newly generates an individual IV from an individual IV in the previous parent generation, using at least one of the techniques of crossover and mutation, and thus generates a population 84 that is an aggregate of the newly generated individual IV and the individual IV maintained in the parent generation, that is, an individual IV formed by replicating the individual IV of the parent generation. In short, each of the plurality of image processing sequences Sq forming the sequence set newly generated from the second generation onward is generated by replication, crossover, or mutation, based on the image processing sequence generated in the previous routine, that is, the image processing sequence Sq of the parent generation.

The gene translation unit 34 refers to a gene table 82, described later, that is stored in the storage device 70, thus translates each gene of the individual IV, and generates the image processing sequence Sq expressed as a tree structure. The gene table 82 is a table prescribing the image processing filter corresponding to each numerical range of the numerical value of a gene, and the coupling relationship between the sequence elements.

The selection unit 36 selects, from learning data 74 formed of a plurality of learning sets SM where one learning set SM is a combination of a learning image LM prepared in advance and a target image TM, a smaller number of learning sets SM than the plurality of learning sets SM. The learning data 74 is stored in the storage device 70. Details of the learning data 74 will be described later.

The image processing unit 40 inputs the learning image LM in the learning set SM selected by the selection unit 36 to the image input layer and performs image processing, according to each of the plurality of image processing sequences Sq generated by the gene translation unit 34, and outputs the output image PM, which is the image after the image processing, from the image output layer for each of the plurality of image processing sequences Sq, and thus generates the output image PM. The image processing unit 40 also inputs an inspection subject image to the image input layer and performs image processing, using the specified image processing sequence DSq stored in the storage device 70, and outputs the output image PM, which is the image after the image processing, from the image output layer, and thus generates the output image PM.

The calculation unit 42 compares the output image PM generated by the image processing unit 40 and the target image TM associated with the learning image LM serving as the base of the output image PM, that is, the target image TM forming one learning set SM with the learning image LM, and calculates an evaluation value EV indicating a degree of similarity SD. For example, the calculation unit 42 compares the output image PM and the target image TM associated with the learning image LM serving as the base of the output image PM, for each of the plurality of image processing sequences Sq represented by each individual IV of the population of one generation G. The calculation unit 42 then calculates the evaluation value EV indicating the degree of similarity SD between the output image PM and the target image TM. When a plurality of learning images LM are image-processed according to one image processing sequence Sq and a plurality of output images PM are thus generated, the evaluation value EV corresponding to each output image PM is calculated and the statistic of the evaluation values EV is calculated as the final evaluation value EV. As the statistic of the evaluation values EV, a value such as the average value or the median value is used. In this embodiment, the average value is used as the statistic.

The evaluation value EV may be an index value indicating the degree of similarity SD between two images. For example, one of the mean squared error (MSE), the peak signa-to-noise ratio (PSNR), and the structural similarity (SSIM) can be used. When the MSE is used as the evaluation value EV, the degree of similarity SD between the output image PM and the target image TM becomes higher as the MSE value becomes lower. That is, the reciprocal of the MSE indicates the degree of similarity SD. When the PSNR is used as the evaluation value EV, the degree of similarity SD between the output image PM and the target image TM becomes higher as the PSNR becomes higher. That is, the PSNR indicates the degree of similarity SD. When the SSIM is used, for example, an image is divided into small areas and the MSSIM (mean SSIM), which is the average value of the SSIM calculated for each small area, is used as the evaluation value EV. When the MSSIM is used as the evaluation value EV, the degree of similarity SD becomes higher as the MSSIM becomes higher. That is, the MSSIM indicates the degree of similarity SD. The "degree of simi-larity SD" may also be referred to as the "similarity degree SD".

The specification unit 46 specifies a subject image processing sequence TSq, which is the image processing sequence Sq having the highest degree of similarity SD, of the plurality of evaluation values EV corresponding respectively to the plurality of image processing sequences Sq. The specification unit 46 also specifies the subject image processing sequence TSq satisfying a predetermined reference condition for acquiring a desired image after the image processing, as the specified image processing sequence DSq. The specified image processing sequence DSq is stored in the storage device 70. Details of the method for specifying the specified image processing sequence DSq will be described later.

The display control unit 60 causes the display unit 160 to display various information. The display control unit 60 causes the display unit 160 to display, for example, the specified image processing sequence DSq, the processed image which has been image-processed according to the image processing sequence Sq represented by the individual IV, the target image TM, and the evaluation value EV.

Figures 2, 3:
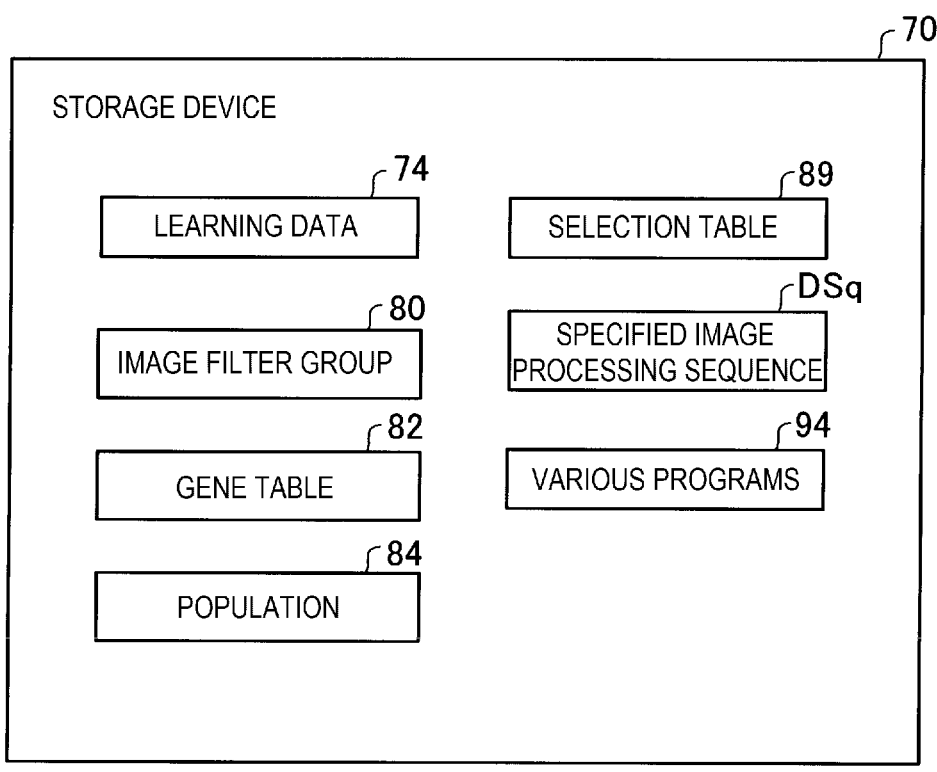
FIG. 2 explains a storage device.
FIG. 3 shows an example of a learning data.

FIG. 2 explains the storage device 70. The storage device 70 stores the learning data 74, an image filter group 80, the gene table 82, the population 84, a selection table 89, the specified image processing sequence DSq, and various programs 94. The specified image processing sequence DSq is the image processing sequence Sq determined as satisfying the predetermined reference condition by the specification unit 46. The specified image processing sequence DSq is expressed, for example, by layer identifiers identifying a plurality of image processing filters, which are a plurality of image processing layers, and the order of the layer identifiers, that is, the coupling relationship. The various programs 94 are programs executed by the processor 25. The selection table 89 is a table used by the selection unit 36 to select the learning set SM. Details of the selection table 89 will be described later.

FIG. 3 shows an example of the learning data 74. The learning data 74 has a plurality of learning sets SM, each learning set SM being formed of (i) a learning image LM, which is a subject of image processing according to the image processing sequence Sq, and (ii) a desired target image TM associated with the learning image LM. In this embodiment, eight learning sets SM are prepared as the learning sets SM provided in the learning data 74. The learning image LM is, for example, an image of a circuit board, which is an industrial product. The target image TM is, for example, a binarized image where a defect part DA is expressed as a black image whereas the other parts are expressed as a white image. The target image TM is gen-erated, for example, by the user setting the defect part DA to be a black image and setting the other parts to be a white image, with reference to the learning image LM where the position of the defect part is specified in advance. The plurality of learning sets SM are formed of a plurality of learning sets SM having an image with the defect part DA, and a plurality of learning sets SM having a plurality of images representing a good-quality product, which are images without including the defect part DA. The plurality of learning images LM are images of circuit boards of the same type with different serial numbers, picked up by the image pickup device 200. Each learning set SM is given an identification number TID. The learning set SM shown in FIG. 3 is given "T01" as the identification number TID.

The image filter group 80 shown in FIG. 2 is an aggregate of a plurality of image filters to be candidates for the sequence elements of the image processing sequence Sq. The image filter may be an average value filter, a maximum value filter, a minimum value filter, a binary value filter, a moving average filter, a Laplacian filter, a Gaussian filter, a Sobel filter, a gamma correction filter, a filter that combines two images together into one image, and the like. Image processing filters of the same type having different kernel sizes or coefficients from each other are stored as different image processing filters in the image filter group 80.

The gene table 82 is a table showing the coupling rela-tionship between candidate sequence elements of the image processing sequence Sq, and the correspondence with the type of the image processing filter corresponding to the numerical value represented by the gene.

Figures 4, 5:
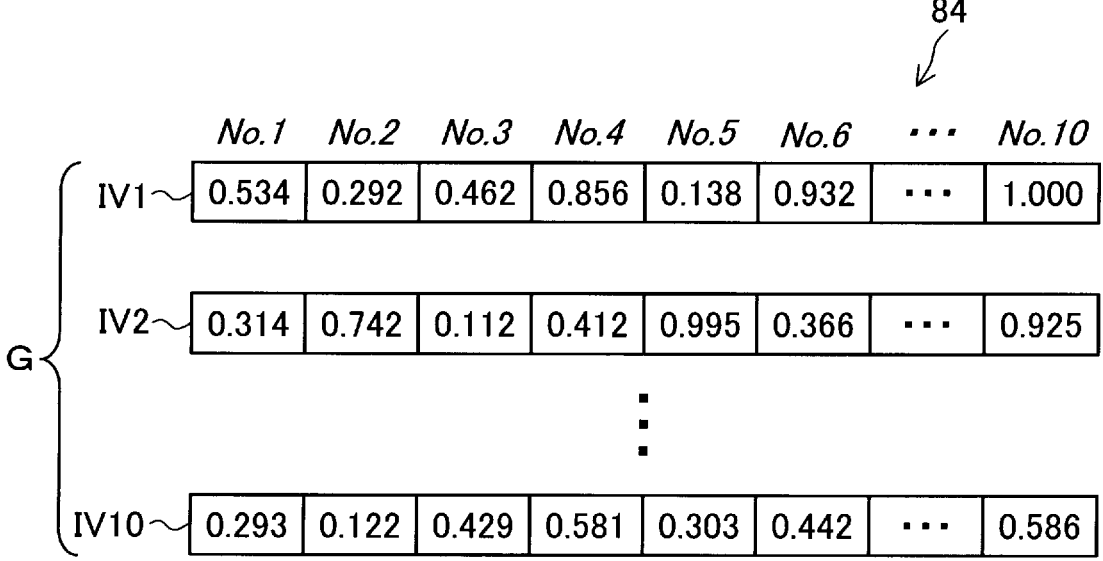
FIG. 4 explains a gene table.
FIG. 5 explains a population of one generation.

FIG. 4 explains the gene table 82. In the description below, to facilitate the understanding, it is assumed that the image filter group 80 is formed of five image processing filters FtA to FtE. In practice, more than five image processing filters are stored in the image processing filter group. In the gene table 82, the number of inputs, the number of outputs, and the range of appearance are prescribed for each filter type representing the type of the image processing filter. The filter type is an identifier identifying each image processing filter of the image filter group 80, or the image input layer. In FIG. 4, the image input layer is represented by a filter type "in". The number of inputs represents the number of sequence elements coupled to the input side of the image processing filter or the image input layer. When the number of inputs is "2", data outputted from two sequence elements are inputted to the image processing filter. The number of outputs represents the number of sequence elements coupled to the output side of the image processing filter. In this embodiment, all the numbers of outputs are "1" and the image processing layer and the image input layer are coupled to one output-side sequence element.

The range of appearance in the gene table 82 prescribes the range of a numerical value VG of the gene. In this embodiment, the numerical values from 0 to 1 are evenly divided into six parts so that the image processing filters appear randomly at substantially equal probabilities in the image processing sequence Sq. For example, when the numerical value VG of the gene is a value equal to or greater than 0 and smaller than 0.167, the image processing filter FtA is allocated to this gene.

The population 84 shown in FIG. 2 is an aggregate of a plurality of individuals IV of one generation G generated by the individual generation unit 32. FIG. 5 explains the population 84 of one generation G. In this embodiment, an example where ten individuals IV1 to IV10 are generated in one generation G is described. In each of the individuals IV1 to IV10, a plurality of loci where genes are arranged are sequenced one-dimensionally. The individuals IV1 to IV10 have the same gene length. Each of the individuals IV1 to IV10 is formed by sequencing genes in order at the loci of No. 1 to No. 10. The individual generation unit 32 arranges a gene expressed by a numerical value down to the third decimal place from 0 to 1, at each locus. That is, in this embodiment, the value that a gene can have at each locus is a numerical value equal to or greater than 0 and equal to or smaller than 1 and down to the third decimal place.

Figures 6, 7:
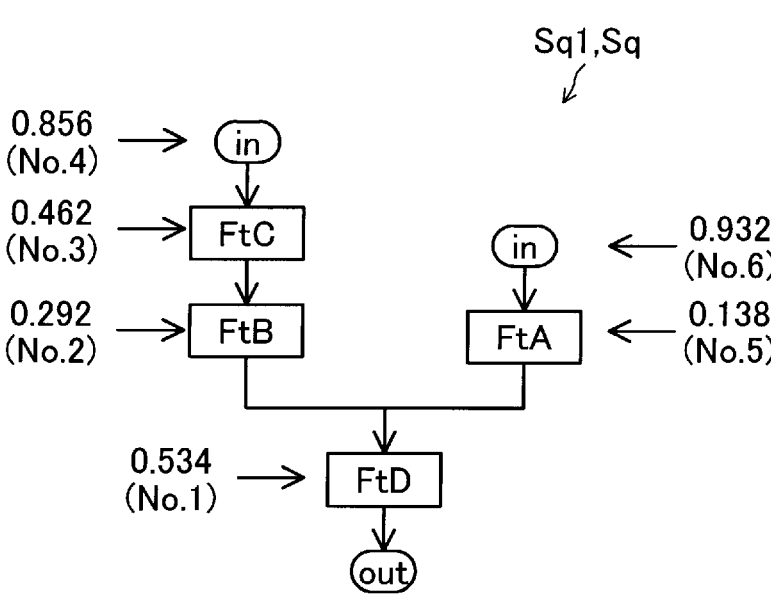
FIG. 6 shows a tree-structured image processing sequence generated by a gene translation unit.
FIG. 7 is a flowchart showing processing executed by a generation device.

Before explaining FIG. 2 further, the processing of generating the image processing sequence Sq by the gene translation unit 34 will be described, using FIG. 6. FIG. 6 shows the image processing sequence Sq having a tree structure generated by the gene translation unit 34. The image processing sequence Sq shown in FIG. 6 is an image processing sequence Sq1 generated based on the individual IV1 shown in FIG. 5.

The gene translation unit 34 generates the image processing sequence Sq having a tree structure in order from the side of an image output layer "out", using the individual IV, the gene table 82, and the image filter group 80. First, the gene translation unit 34 sets the image output layer "out" as a terminal node and couples the sequence elements in the order of sequence of the genes of the individual IV. The coupling of the sequence elements is executed according to a predetermined coupling rule. In this embodiment, the image processing sequence Sq is generated according to a rule such that the sequence elements are arranged preferentially from the terminal node side in the order of sequence of the genes and preferentially at the coupling point on the left side shown in FIG. 6 over the coupling point on the right side. That is, the image processing layer or the image input layer "in" is arranged from the side of the image output layer "out" in the order of sequence of the genes, and when the input side is divided into a plurality of sections, the left side is prioritized until the left-side sequence becomes the image input layer "in". In this embodiment, the number of inputs of the image output layer "out" is preset to be "1".

The gene translation unit 34 refers to "0.534", which is the numerical value VG of the gene of No. 1 of the individual IV1, and the gene table 82, and thus specifies that "0.534" is within the range of appearance of the image processing filter FtD. Thus, the image processing filter FtD is coupled to the input side of the image output layer "out". Next, the gene translation unit 34 specifies that the number of inputs of the image processing filter FtD is "2", referring to the gene table 82, and thus arranges two sequence elements at the input side of the image processing filter FtD. Specifically, the gene translation unit 34 arranges the sequence element corresponding to the gene of No. 2 of the individual IV1, at the input-side coupling point on the left side shown in FIG. 6. That is, the gene translation unit 34 refers to "0.292", which is the numerical value VG of the gene of No. 2, and the gene table 82, and thus specifies that "0.292" is within the range of appearance of the image processing filter FtB. Thus, the image processing filter FtB is arranged at the input-side coupling point on the left side of the image processing filter FtD.

Next, the gene translation unit 34 specifies that the number of inputs of the image processing filter FtB is "1", referring to the image processing filter FtB represented by the gene of No. 2 and the gene table 82, and thus arranges one sequence element at the input side of the image processing filter FtB. Specifically, the gene translation unit 34 refers to "0.462", which is the numerical value VG of the gene of No. 3, and the gene table 82, and thus specifies that "0.462" is within the range of appearance of the image processing filter FtC. Thus, the image processing filter FtC is arranged at the input-side coupling point of the image processing filter FtB represented by the gene of No. 2.

Next, the gene translation unit 34 specifies that the number of inputs of the image processing filter FtC is "1", referring to the image processing filter FtC represented by the gene of No. 3 and the gene table 82, and thus arranges one sequence element at the input side of the image processing filter FtC. Specifically, the gene translation unit 34 refers to "0.856", which is the numerical value VG of the gene of No. 4, and the gene table 82, and thus specifies that "0.856" is within the range of appearance of the image input layer "in". Thus, the image input layer "in" is arranged at the input-side coupling point of the image processing filter FtC represented by the gene of No. 3. Then, the generation of the sequence on the left side of the image processing sequence Sq shown in FIG. 6 ends.

Subsequently, the gene translation unit 34 arranges the sequence element corresponding to the gene of No. 5 of the individual IV1, at the input-side coupling point on the right side shown in FIG. 6. That is, the gene translation unit 34 refers to "0.138", which is the numerical value VG of the gene of No. 5, and the gene table 82, and thus specifies that "0.138" is within the range of appearance of the image processing filter FtA. Thus, the image processing filter FtA is arranged at the input-side coupling point on the right side of the image processing filter FtD.

Also, the gene translation unit 34 specifies that the number of inputs of the image processing filter FtA is "1", referring to the image processing filter FtA represented by the gene of No. 5 and the gene table 82, and thus arranges one sequence element at the input side of the image processing filter FtA. Specifically, the gene translation unit 34 refers to "0.932", which is the numerical value VG of the gene of No. 6, and the gene table 82, and thus specifies that "0.932" is within the range of appearance of the image input layer "in". Thus, the image input layer "in" is arranged at the input-side coupling point of the image processing filter FtA represented by the gene of No. 5. Then, the generation of the sequence on the right side of the image processing sequence Sq shown in FIG. 6 ends. As described above, when all the input-side sequence elements, which are the input-side coupling points coupled to the output-side sequence element, become the image input layer "in", the gene translation unit 34 ends the processing of generating the image processing sequence Sq even if not all the genes of the individual IV1 are used. When all the genes of the individual IV1 are used and not all the input-side sequence elements, which are the input-side coupling points, are the image input layer "in", the gene translation unit 34 sets the image input layer "in" to the remaining input-side sequence element that is not coupled, and thus ends the generation of the image processing sequence Sq.

The image processing sequence Sq1 represented by the individual IV1 has two image input layers "in". The image inputted to one image input layer "in" is image-processed by the image processing filter FtC and subsequently image-processed by the image processing filter FtB, and thus a first processed image is generated. The image inputted to the other image input layer "in" is image-processed by the image processing filter FtA and a second processed image is generated. The first processed image and the second processed image are image-processed by the image processing filter FtD. The final processed image is outputted by the image output layer "out".

As described above, a plurality of image processing sequences Sq can be easily represented, based on the individual IV and the gene table 82.

FIG. 7 is a flowchart showing processing executed by the generation device 20. This processing includes a generation process for the specified image processing sequence DSq, which is step S10, and a use processing process using the specified image processing sequence DSq, which is step S50 executed after step S10. The generation process for the specified image processing sequence DSq is executed by the sequence generation function of the generation device 20. The use processing process is executed by the image processing function of the generation device 20.

FIG. 8 is a flowchart showing details of the generation process of step S10. FIG. 9 is a first chart for explaining the generation process of step S10. FIG. 10 is a second chart for explaining the generation process of step S10.

First, as shown in FIG. 8, in step S90, the storage device 70 stores a plurality of image processing filters as the image filter group 80. Step S90 is executed by the user inputting, to the generation device 20, a plurality of image processing filters to be candidates used in the specified image processing sequence DSq. In step S91, the learning data 74 formed of a plurality of learning sets SM, each learning set SM being formed of the learning image LM and the target image TM, is prepared. The prepared learning data 74 is stored in the storage device 70. Step S91 is executed by the user inputting a plurality of learning sets SM to the generation device 20. The order of step S90 and step S91 is not limited to this example.

Next, in step S92, the individual generation unit 32 generates the population 84 formed of a plurality of individuals IV for a current generation Gm. As described with reference to FIG. 5, the population 84 is formed of the individuals IV1 to IV10. The generated population 84 is stored in the storage device 70.

Next, in step S94, the selection unit 36 selects a smaller number of learning sets SM than the number of the plurality of learning sets SM of the learning data 74, from among the plurality of learning sets SM of the learning data 74. In this embodiment, in step S94, two learning sets SM are selected. As shown in FIG. 9, in the current generation Gm, which is the present routine, two learning sets SM having an identification number T02 and an identification number T04, from among identification numbers T01 to T08, are selected. Step S94 may be executed before step S92 or may be executed after step S104, described later. Details of step S94 will be described later.

Next, as shown in FIG. 8, in step S105, the gene translation unit 34 translates each gene of each individual IV by referring to each individual IV and the gene table 82, and thus generates the image processing sequence Sq from each individual IV. That is, step S105 is a process of generating a sequence set formed of a plurality of image processing sequences Sq with different combinations.

Next, in step S106, the image processing unit 40 executes first image processing of image-processing the learning image LM according to each of the plurality of image processing sequences Sq of the current generation Gm, which is the present routine, and thus generating the output image PM, which is an image-processed image, for each of the plurality of image processing sequences Sq. The output image PM is stored in the storage device 70.

After step S106, the calculation unit 42 in step S107 compares the output image PM outputted through the first image processing of step S106 and the target image TM associated with the learning image LM serving as the base of the output image PM, for each of the plurality of image processing sequences Sq of the current generation Gm. In step S107, the calculation unit 42 calculates the evaluation value EV indicating the degree of similarity SD between the output image PM and the target image TM. As shown in FIG. 9, in step S107, the evaluation value EV in the case of using the image processing sequence Sq represented by each of the individuals IV of the current generation Gm given the identification numbers ID of "I001" to "I010" with respect to the learning sets SM having the identification numbers TID of "T02" and "T04", selected in step S94, is calculated. The calculated evaluation value EV is stored in association with the individual IV and the learning set SM, in the storage device 70. For example, the evaluation value EV in the case of using the image processing sequence Sq represented by the individual IV given the identification number ID of "I010" with respect to the learning set SM having the identification number TID of "T02" is "0.843".

Also, as shown in FIG. 9, when a plurality of learning sets SM are selected in step S94, the calculation unit 42 in step S107 calculates a statistic of the evaluation value EV for each selected learning set SM with respect to each image processing sequence Sq, as the final evaluation value EV. In this embodiment, the calculation unit 42 calculates the average value of the evaluation values of the selected two learning sets SM, as the final evaluation value EV. In another embodiment, the calculation unit 42 may calculate a statistic such as the median value, the mode value, or the maximum value, of a plurality of evaluation values EV for a plurality of selected learning sets SM with respect to each image processing sequence Sq, as the final evaluation value EV. The final evaluation value EV is also referred to as an evaluation value FEV. In this embodiment, an index of the evaluation value EV having such a relationship that the degree of similarity SD becomes higher as the evaluation value FEV becomes higher, is used.

As shown in FIG. 8, in step S109, the specification unit 46 specifies the subject image processing sequence TSq, which is the image processing sequence Sq with the highest degree of similarity SD, of the plurality of evaluation values FEV corresponding respectively to the plurality of image processing sequences Sq corresponding to the individuals IV. In the example shown in FIG. 9, the specification unit 46 specifies the image processing sequence Sq having the individual ID of "I001" as the subject image processing sequence TSq because this image processing sequence Sq has the highest evaluation value FEV and the highest degree of similarity SD.

As shown in FIG. 8, in step S110 after step S109, the image processing unit 40 executes second image processing of image-processing the learning image LM of each of the learning sets SM that are more than the number of the learning sets SM selected in step S94 and that are two sets or more including the learning sets SM selected in step S94, according to the subject image processing sequence TSq, and thus generating a subject output image PM as the output image PM. In this embodiment, in step S110, the second image processing is executed on all of the plurality of learning sets SM of the learning data 74 prepared in step S91, and the subject output image PM is thus generated. In step S110, for the learning image LM of the learning set SM with which the subject output image PM is already generated in step S106, the subject output image PM generated in step S106 may be used and therefore the subject output image PM may be generated without performing the image processing according to the image processing sequence Sq again. Thus, the time of the image processing can be reduced and therefore the processing time of the generation process can be reduced.

In step S111 after step S110, the calculation unit 42 compares the subject output image PM for each learning image LM generated in step S110 and the target image TM associated with the learning image LM serving as the base of the subject output image PM, and calculates a subject evaluation value EV as the evaluation value EV. As for the evaluation value EV already calculated in step S107, the evaluation value EV calculated in step S107 may be used as the subject evaluation value EV and the subject evaluation value EV may thus be calculated. Also, in step S110, for the learning image LM of the learning set SM corresponding to the valuation value EV calculated in step S107, the image processing according to the image processing sequence Sq may be not performed again. Thus, the time of the image processing and the time for calculating the subject evaluation value EV can be reduced and therefore the processing time of the generation process can be reduced. As shown in FIG. 9, as step S111 is executed, the subject evaluation values EV for all the eight learning sets SM given the identification numbers TID of "T01" to "T08" in the subject image processing sequence TSq corresponding to the identification ID of the individual IV of "I001" are calculated.

Next, as shown in FIG. 8, in step S112, the specification unit 46 executes determination processing of determining whether the subject image processing sequence TSq satisfies a predetermined reference condition or not, using the subject evaluation value EV calculated in step S111. Specifically, the specification unit 46 calculates the statistic of the subject evaluation values EV of the plurality of learning sets SM calculated in step S111. The statistic may be the average value, the median value, the mode value, the maximum value or the like. In this embodiment, the statistic of the subject evaluation values EV is the average value. In the determination processing, when the degree of similarity SD represented by the statistic is equal to or higher than a predetermined threshold, the specification unit 46 determines that the reference condition is satisfied. Specifically, when the statistic has such a value that the degree of similarity SD is equal to or higher than the threshold, the specification unit 46 determines that the reference condition is satisfied. In this embodiment, when the average value, which is the statistic, is equal to or higher than an evaluation reference value, the degree of similarity SD is equal to or higher than the threshold and therefore the specification unit 46 determines that the reference condition is satisfied.

As described above, the subject evaluation value EV is calculated for all the learning sets SM, and whether the subject image processing sequence TSq satisfies the reference condition or not is determined, using the calculated subject evaluation value EV. Therefore, a desired specified image processing sequence DSq suitable for various images can be acquired. Also, as described above, whether the reference condition is satisfied or not is determined, based on the statistic of the subject evaluation values EV. Therefore, whether the reference condition is satisfied or not can be determined, based on a plurality of subject evaluation values corresponding to a plurality of learning sets SM. Thus, whether or not the subject image processing sequence TSq is a sequence that enables such image processing as to make various learning images LM closer to the target image TM, can be determined accurately.

When it is determined in the determination processing of step S112 that the subject image processing sequence TSq satisfies the reference condition, the specification unit 46 outputs the subject image processing sequence TSq satisfying the reference condition, as the specified image processing sequence DSq. The outputted specified image processing sequence DSq is stored in the storage device 70.

Meanwhile, when it is determined in the determination processing of step S112 that the subject image processing sequence TSq does not satisfy the reference condition, processing from step S92 onward in the next routine is executed. That is, the process of generating a sequence set, the process of selecting the learning set SM, the process of generating the output image PM, the process of calculating the evaluation value EV, the process of specifying the subject image processing sequence, the process of calculating the subject evaluation value, and the process of determining whether the reference condition is satisfied or not, are repeatedly executed until the subject image processing sequence TSq satisfies the reference condition.

In step S92 in the next routine after "NO" is given as the result of the determination in step S112, the individual generation unit 32 generates a population 84 of a generation Gn in the present routine, using the population 84 of the generation Gm generated in the previous routine. The population 84 of the generation Gn is generated by replication, crossover or mutation of the individual IV of the previous generation Gm. Specifically, the individual generation unit 32 replicates the individual IV of the image processing sequence Sq that is the base of the calculation of the evaluation value FEV satisfying the evaluation condition indicating that the degree of similarity SD is high, of the evaluation values FEV for each of the plurality of image processing sequences Sq calculated in the previous routine. As for the individual IV of the image processing sequence Sq that does not satisfy the evaluation condition, of the evaluation values FEV for each of the plurality of image processing sequences Sq calculated in the previous routine, the individual generation unit 32 performs crossover or mutation on the individual IV satisfying the evaluation condition and thus generates a new individual IV. The replicated individual IV, and the individual IV newly generated by crossover or mutation, form the population 84 of the generation Gn. That is, the individual generation unit 32 newly generates a sequence set having a combination of a plurality of image processing sequences Sq that is different from the combination in the previously generated sequence set. The newly generated sequence set is used for the image processing of the learning set SM that is newly selected in the present routine. The evaluation condition is that the degree of similarity SD is the J-th from the top, of the plurality of individuals IV of the parent generation Gm used in the previous routine. "J" is an integer equal to or greater than 1. In this embodiment, "J" is "4". The evaluation condition may be that the degree of similarity SD indicated by the final evaluation value FEV, which is the average value, of the plurality of individuals IV of the parent generation Gm used in the previous routine, is equal to or higher than a replication threshold. Thus, the image processing sequence Sq satisfying the evaluation condition indicating that the degree of similarity SD is high is left as it is, and the image processing sequence Sq that does not satisfy the evaluation condition is replaced by a new image processing sequence Sq. Therefore, a desired specified image processing sequence DSq used to image-process an image to acquire an intended image can be acquired efficiently.

As shown in FIG. 10, in the generation Gn, four individuals IV with the individual ID of "I001", the individual ID of "I002", the individual ID of "I004", and the individual ID of "I008" having the highest four degrees of similarity SD, of the previous generation Gm, are replicated, and crossover or mutation is performed on the replicated four individuals IV to generate the remaining six individuals IV. In the generation Gn in the present routine, the selection unit 36 in step S94 selects the learning sets SM with the identification numbers TID of "T03" and "T08". In the generation Gn in the present routine, the specification unit 46 in step S109 specifies the image processing sequence Sq represented by the individual IV with the individual ID of "I008", as the subject image processing sequence TSq.

As described above, in step S92 in the next routine, the individual generation unit 32 generates a population 84 representing a sequence set including the image processing sequence Sq that is the base of the calculation of the evaluation value FEV satisfying the evaluation condition indicating that the degree of similarity SD is high, of the plurality of evaluation values FEV calculated in the previous routine, and the image processing sequence Sq that is different from the image processing sequence Sq forming the sequence set in the previous routine.

Figures 11, 12:
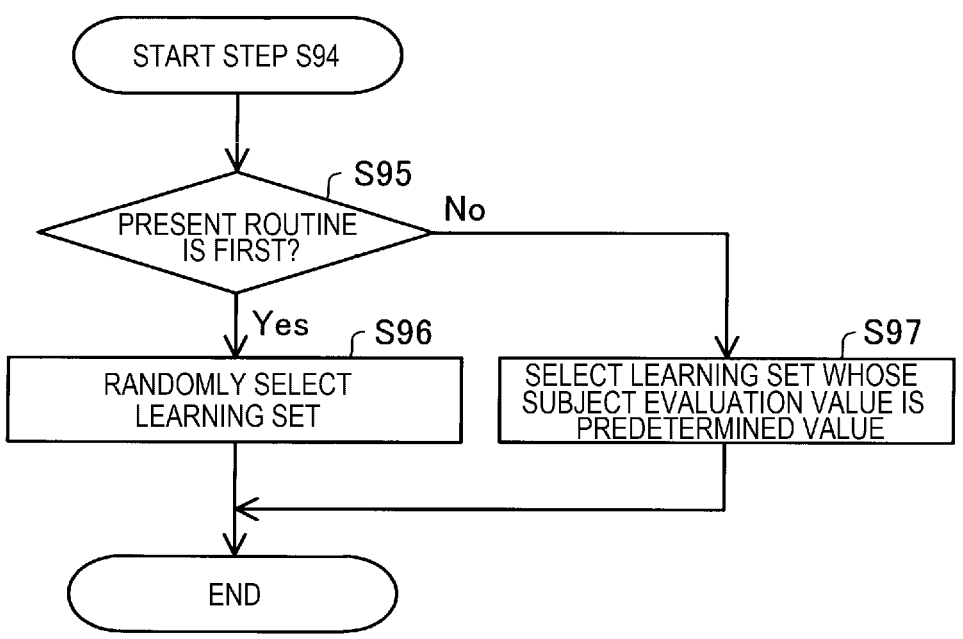
FIG. 11 is a flowchart showing details of step S94 in FIG. 8.
FIG. 12 explains steps S96 and S97 in FIG. 11.

FIG. 11 is a flowchart showing details of step S94 in FIG. 8. FIG. 12 explains steps S96 and S97 in FIG. 11. When the selection unit 36 selects a predetermined number of learning sets SM from among a plurality of learning sets SM of the learning data 74 in step S94, the following processing is executed. First, the selection unit 36 in step S95 determines whether the present routine is the first routine or not. When the present routine is the first routine, the selection unit 36 in step S96 randomly selects two learning sets SM from among the plurality of learning sets SM of the learning data 74. Meanwhile, when the present routine is not the first routine but is the second or subsequent routine, the selection unit 36 in step S97 sets a higher probability of selection at which a learning set SM having a predetermined value is selected, from among the subject evaluation values EV of the two or more learning sets SM calculated by the calculation unit 42 in the previous routine, in this embodiment, all the learning sets SM of the learning data 74, and thus executes selection processing and selects a new learning set SM. In this embodiment, the predetermined value used in step S97 refers to such a value that the degree of similarity SD indicated by the subject evaluation value EV is lower. That is, in step S97, the selection unit 36 sets a higher probability of selection at which the learning set SM is selected, as the degree of similarity SD indicated by each of the subject evaluation values EV of the two or more learning sets SM calculated by the calculation unit 42 in the previous routine, in this embodiment, all the learning sets SM of the learning data 74, becomes lower. Since the probability of selection is made higher for the learning set SM where the degree of similarity SD has a lower value, the probability of the learning set SM being selected in the next routine increases and therefore a desired specified image processing sequence DSq suitable for various images can be acquired by the generation process.

A specific example of steps S96 and S97 shown in FIG. 11 will now be described, using FIG. 12. In the selection table 89, the identification number TID of the learning set SM, and a selection range that is set for each identification number TID, are prescribed. For each identification number TID, the selection range is set in such a way as not to overlap the other selection ranges. The selection unit 36 randomly generates two numerical values that are selection values SR down to the third decimal place from 0 to 1. The selection unit 36 then determines which selection range in the selection table 89 the selection values SR are present within, and selects the learning sets SM corresponding to the selection ranges. For example, in the example shown in FIG. 12, when the selection values SR are "0.123" and "0.911", the learning sets SM with the identification numbers TID of "T01" and "T08" are selected. When the selected two learning sets SM are the same, the selection unit 36 maintains one selection value SR and randomly generates the other selection value SR until a learning set SM that is different from the learning set SM decided by the one selection value SR is selected.

The selection unit 36 can change an upper limit value and a lower limit value representing a width of the selection range for each identification number TID and thus can change the probability of selection at which each learning set SM is selected. For example, in step S96 in FIG. 11, the selection unit 36 sets the upper limit value and the lower limit value in such a way that the width of the selection range for each of the identification numbers TID of "T01" to "T08" is uniform so that all the learning sets SM are randomly selected. Meanwhile, in step S97 in FIG. 11, the selection unit 36 increases the width of the selection range to increase the selection probability for the learning set SM that is the base of the calculation, as the degree of similarity SD of the subject evaluation value EV calculated in the previous routine becomes lower. For example, the selection unit 36 sets the selection range corresponding to each identification number TID in such a way that the width is in proportion to the magnitude of the reciprocal of the degree of similarity SD of the subject evaluation value EV calculated in the previous routine.

FIG. 13 is a flowchart showing the use processing process. The use processing process is executed after the specified image processing sequence DSq is specified by the generation process in FIG. 8. First, in step S200, the storage device 70 stores a plurality of image processing filters accepted by the input unit 150, as the image filter group 80. The plurality of image processing filters of the image filter group 80 stored in the use processing process may be only the image processing filters used in the specified image processing sequence DSq. When the use processing process and the generation process in FIG. 8 are executed by the same generation device 20, step S200 can be omitted and the image filter group 80 stored in the storage device 70 in step S90 shown in FIG. 8 can be used.

Next, in step S201, the storage device 70 stores the specified image processing sequence DSq outputted in step S113 in FIG. 8. The order of step S200 and step S201 is not limited to the above example.

Next, in step S203, the image processing unit 40 reads out and thus acquires an image that is stored in the storage device 70 via the input unit 150 and that is a subject of image processing according to the specified image processing sequence DSq. The image acquired in step S203 is, for example, a picked-up image of a subject of the same type as the learning image LM. When there are a plurality of images to be subjects of image processing, the image processing unit 40 may read out and thus acquire one of a plurality of images stored in advance in the storage device 70 or may acquire a subject image from the image pickup device 200 each time at the timing of executing image processing, described later.

Next, in step S204, the image processing unit 40 executes the image processing using the specified image processing sequence DSq, on the image acquired in step S203. That is, the image processing unit 40 executes the image processing of the image, using the image processing filter stored in the image filter group 80 in the storage device 70, according to the order represented by the specified image processing sequence DSq.

Next, in step S205, the output image PM, which is the image after the image processing using the specified image processing sequence DSq, is outputted. Step S205 is executed, for example, by storing the output image PM in the storage device 70 or by displaying the output image PM on the display unit 160.

Next, in step S206, the image processing unit 40 determines whether to continue the image processing using the specified image processing sequence DSq or not. For example, when information indicating the continuation of the image processing is inputted by the user or when an unprocessed image that is a subject of the image processing is left in the storage device 70, the image processing unit 40 determines that the image processing is to be continued. When the image processing is to be continued, the processing from step S203 onward is executed again. Meanwhile, when information indicating the end of the image processing is inputted by the user or when an unprocessed image that is a subject of the image processing is not left in the storage device 70, the image processing unit 40 ends the use processing process.

According to the above embodiment, in the generation process shown in FIG. 8, a smaller number of learning sets SM than the plurality of learning sets SM are selected, and whether the subject image processing sequence TSq satisfies the predetermined reference condition or not is determined, using the selected learning set SM. Thus, the amount of computation for acquiring the specified image processing sequence DSq can be reduced and therefore the processing time for acquiring the specified image processing sequence DSq can be reduced. Also, when selecting the learning set SM, the probability of selection of the learning set SM having a predetermined value, of the subject evaluation values in the previous routine, is increased. Thus, the probability that the learning set SM selected in each routine tends to be the learning set SM having images with similar feature values can be reduced. Therefore, a desired specified image processing sequence DSq suitable for various images can be acquired.

B. Other Embodiments

B-1. Other Embodiment 1

In the above embodiment, the image processing of the learning image LM according to a plurality of image processing sequences Sq represented by a plurality of individuals IV belonging to one generation G is sequentially executed by one generation device 20. However, the image processing may be executed in parallel, using a plurality of generation devices 20.

B-2. Other Embodiment 2

In the above embodiment, the image processing sequence Sq is represented by the individual IV and the gene table 82. However, this is not limiting. For example, the image processing sequence Sq may be represented by a plurality of sequence elements and a table prescribing the coupling relationship between the sequence elements.

B-3. Other Embodiment 3

In the above embodiment, the number of learning sets SM selected in step S94 in FIG. 8 is two. However, this is not limiting. This number may be one or may differ from one routine to another.

B-4. Other Embodiment 4

In the above embodiment, the selection unit 36 increases the probability of selection in the next routine, for the learning set SM having a lower value, of the degree of similarity SD indicated by each of a plurality of subject evaluation values FEV calculated in the previous routine. However, this it not limiting. For example, the selection unit 36 may select, in the next routine, the learning set SM having a predetermined value or a lower value, of the degree of similarity SD indicated by each of a plurality of subject evaluation values FEV calculated in the previous routine, or may select, in the next routine, the learning sets SM having the degree of similarity SD up to the K-th from the bottom, where K is an integer equal to or greater than 1.

B-5. Other Embodiment 5

In the above embodiment, the calculation unit 42 image-processes the learning image LM according to each of a plurality of image processing sequences Sq and the subject image processing sequence TSq, generates the output image PM and the subject output image PM, compares these output images with the target image TM associated with the learning image LM, and calculates the evaluation values EV and the subject evaluation values EV. However, the evaluation value EV and the subject evaluation values EV already calculated in a generation preceding the current generation may be used for the calculation. Thus, the time of the image processing and the time for calculating the evaluation value EV and the subject evaluation values EV can be reduced and therefore the processing time of the generation process can be reduced.

C. Other Aspects

The present disclosure is not limited to the above embodiment and can be implemented according to various aspects without departing from the spirit and scope of the present disclosure. For example, the present disclosure can be implemented according to the aspects described below. A technical feature in the embodiment corresponding to a technical feature in the aspects described below can be replaced or combined where appropriate in order to solve a part or all of the problems of the present disclosure or in order to achieve a part or all of the effects of the present disclosure. The technical feature can be deleted where appropriate, unless described as essential in the present specification.

(1) According to a first aspect of the present disclosure, a method for generating an image processing sequence is provided. The method for generating the image processing sequence includes: (a) preparing a plurality of learning sets, the learning set including a learning image and a target image associated with the learning image; (b) generating a sequence set formed of a plurality of image processing sequences, the image processing sequence representing a combination of (i) an image input layer to input an image, (ii) at least one of a plurality of image processing layers, and (iii) an image output layer to output the image after image processing, as sequence elements, the combination varying between the plurality of the image processing sequences; (c) selecting a smaller number of the learning sets than the plurality of the learning sets, from among the plurality of the learning sets; (d) image-processing the learning image in the learning set selected in the (c), according to each of the plurality of the image processing sequences, and generating an output image that is an image after the image processing for each of the plurality of the image processing sequences; (e) comparing the output image and the target image associated with the learning image serving as a base of the output image, and calculating an evaluation value indicating a degree of similarity between the output image and the target image, for each of the plurality of the image processing sequences; (f) specifying a subject image processing sequence that is the image processing sequence where the degree of similarity is the highest, of a plurality of the evaluation values corresponding respectively to the plurality of the image processing sequences; (g) image-processing the learning image of each of the learning sets that are more than the number of the learning sets selected in the (c), of the plurality of the learning sets, and that are two sets or more including the learning set selected in the (c), according to the subject image processing sequence, thus generating the output image, comparing the output image and the target image associated with the learning image serving as the base of the output image, and calculating a subject evaluation value as the evaluation value; and (h) determining whether the subject image processing sequence satisfies a predetermined reference condition or not, using the subject evaluation value. The method for generating the image processing sequence repeatedly executes the (b) to the (h) until the subject image processing sequence satisfies the reference condition. When selecting the learning set in the (c), a probability of selection of the learning set having a predetermined value, of a plurality of the subject evaluation values corresponding respectively to the two sets or more of the learning sets calculated in the (g) in a previous routine, is increased. According to this aspect, a smaller number of learning sets than the plurality of learning sets are selected, and whether the subject image processing sequence satisfies the predetermined reference condition or not is determined, using the selected learning set. Thus, the amount of computation can be reduced and therefore the processing time for acquiring a desired image processing sequence can be reduced. Also, when selecting a learning set, the probability of selection of the learning set having a predetermined value, of the subject evaluation values in the previous routine, is increased. Thus, the probability that the learning set selected in each routine inclines can be reduced. Therefore, a desired specified image processing sequence suitable for various images can be acquired.

(2) In the above aspect, in the (b), a sequence set including the image processing sequence serving as the base of calculation of the evaluation value satisfying an evaluation condition indicating that the degree of similarity is high, of a plurality of the evaluation values calculated in the (e) in the previous routine, and the image processing sequence that is different from the image processing sequence forming the sequence set of the previous routine, may be generated. According to this aspect, the image processing sequence satisfying the evaluation condition indicating that the degree of similarity is high is left as it is, and the image processing sequence that does not satisfy the evaluation condition is replaced by a new image processing sequence. Thus, a desired image processing sequence can be acquired efficiently.

(3) In the above aspect, in the (g), all of the learning images of the plurality of learning sets prepared in the (a) may be image-processed to output the output image, and the subject evaluation value may be calculated for all of the learning images. According to this aspect, the subject evaluation value is calculated for all of the learning sets, and whether the subject image processing sequence satisfies the reference condition or not is determined, using the calculated subject evaluation value. Therefore, a desired image processing sequence suitable for various images can be acquired.

(4) In the above aspect, in the (h), a statistic of a plurality of the subject evaluation values corresponding to the plurality of learning sets may be calculated, and when the degree of similarity indicated by the statistic is equal to or higher than a predetermined threshold, it may be determined that the reference condition is satisfied. According to this aspect, whether the reference condition is satisfied or not can be determined, based on a plurality of subject evaluation values corresponding to a plurality of learning sets.

(5) In the above aspect, when selecting the learning set in the (c), the probability of selection of the learning set may be made higher as the degree of similarity indicated by each of a plurality of the subject evaluation values corresponding to the two sets or more of the learning sets, calculated in the (g) in the previous routine, becomes lower. According to this aspect, since the probability of selection is made higher for a learning set where the degree of similarity has a lower value, the probability of the learning set being selected in the next routine increases and therefore a desired image processing sequence suitable for various images can be acquired.

(6) In the above aspect, in the (b), each of the plurality of image processing sequences may be represented by an individual formed by sequencing a plurality of genes corresponding to the image input layer and the image processing layer, respectively, and a gene table prescribing a coupling relationship between the sequence elements. According to this aspect, a plurality of image processing sequences can be easily represented, based on the individual and the gene table.

(7) According to a second aspect of the present disclosure, a generation device for an image processing sequence is provided. The generation device includes: a sequence generation unit generating a sequence set formed of a plurality of image processing sequences, the image processing sequence representing a combination of (i) an image input layer to input an image, (ii) at least one of a plurality of image processing layers, and (iii) an image output layer to output the image after image processing, as sequence elements, the combination varying between the plurality of image processing sequences; a selection unit selecting, from among a plurality of learning sets where the learning set is a combination of a learning image prepared in advance and a target image, a smaller number of the learning sets than the plurality of the learning sets; an image processing unit image-processing the learning image in the learning set selected by the selection unit, according to each of the plurality of the image processing sequences, and generating an output image that is an image after the image processing for each of the plurality of the image processing sequences; a calculation unit comparing the output image and the target image forming the learning set with the learning image serving as a base of the output image, and calculating an evaluation value indicating a degree of similarity between the output image and the target image, for each of the plurality of the image processing sequences; and a specification unit specifying a subject image processing sequence that is the image processing sequence where the degree of similarity is the highest, of a plurality of the evaluation values corresponding respectively to the plurality of the image processing sequences. The image processing unit image-processes the learning image of each of the learning sets that are more than the number of the learning sets selected by the selection unit, of the plurality of the learning sets, and that are two sets or more including the learning set selected by the selection unit, according to the subject image processing sequence, and thus generates a subject output image as the output image. The calculation unit compares the subject output image and the target image associated with the learning image serving as the base of the subject output image, and calculates a subject evaluation value as the evaluation value. The specification unit determines whether the subject image processing sequence satisfies a predetermined reference condition or not, using the subject evaluation value. When the subject image processing sequence does not satisfy the reference condition, the selection unit increases a rate of selection of the learning set having a predetermined value, of a plurality of the subject evaluation values corresponding respectively to the two sets or more of the learning sets calculated by the calculation unit, and newly selects the learning set, and the sequence generation unit generates the sequence set that is for the newly selected learning set and that differs from the sequence set which is generated previously. This aspect can achieve effects similar to those of the first aspect.

(8) According to a third aspect of the present disclosure, a computer program is provided. The computer program causes a computer to execute: (a) a sequence generation function of generating a sequence set formed of a plurality of image processing sequences, the image processing sequence representing a combination of (i) an image input layer to input an image, (ii) at least one of a plurality of image processing layers, and (iii) an image output layer to output the image after image processing, as sequence elements, the combination varying between the plurality of the image processing sequences; (b) a function of selecting, from among a plurality of learning sets where the learning set is a combination of a learning image prepared in advance and a target image associated with the learning image, a smaller number of the learning sets than the plurality of the learning sets; (c) a function of image-processing the learning image in the learning set selected by the function (b), according to each of the plurality of the image processing sequences, and generating an output image that is an image after the image processing for each of the plurality of the image processing sequences; (d) a function of comparing the output image and the target image associated with the learning image serving as a base of the output image, and calculating an evaluation value indicating a degree of similarity between the output image and the target image, for each of the plurality of the image processing sequences; (e) a function of specifying a subject image processing sequence that is the image processing sequence where the degree of similarity is the highest, of a plurality of the evaluation values corresponding respectively to the plurality of the image processing sequences; (f) a function of image-processing the learning image of each of the learning sets that are more than the number of the learning sets selected by the function (b), of the plurality of the learning sets, and that are two sets or more including the learning set selected by the function (b), according to the subject image processing sequence, thus generating the output image, comparing the output image and the target image associated with the learning image serving as the base of the output image, and calculating a subject evaluation value as the evaluation value; and (g) a function of determining whether the subject image processing sequence satisfies a predetermined reference condition or not, using the subject evaluation value. The computer program causes the computer to repeatedly execute the function (a) to the function (g) until the subject image processing sequence satisfies the reference condition. The function (b) has a function of increasing a probability of selection of the learning set having a predetermined value, of a plurality of the subject evaluation values corresponding respectively to the two sets or more of the learning sets calculated by the function (f) in a previous routine, when selecting the learning set. This aspect can achieve effects similar to those of the first aspect.

The present disclosure can also be implemented according to various other aspects than the above. For example, the present disclosure can be implemented in the form of a non-transitory storage medium storing the computer program.

What is claimed is:

1. A method for generating an image processing sequence, the method comprising:
   (a) preparing a plurality of learning sets, a learning set of the plurality of learning sets including a learning image and a target image associated with the learning image;
   (b) generating a sequence set formed of a plurality of image processing sequences, the image processing sequence of the plurality of image processing sequences representing a combination of (i) an image input layer to input an image, (ii) at least one of a plurality of image processing layers, and (iii) an image output layer to output the image after image processing, as sequence elements, the combination varying between the plurality of image processing sequences;

(c) selecting a number of learning sets that is smaller than the plurality of learning sets, from among the plurality of learning sets;

(d) image-processing the learning image in the selected number of learning sets selected in the (c), according to each of the plurality of image processing sequences, and generating an output image that is an image after the image processing for each of the plurality of image processing sequences;

(e) comparing the output image and the target image associated with the learning image serving as a base of the output image, and calculating an evaluation value of a plurality of evaluation values indicating a degree of similarity between the output image and the target image, for each of the plurality of image processing sequences;

(f) specifying a subject image processing sequence that is the image processing sequence where the degree of similarity is highest, of the plurality of evaluation values corresponding respectively to the plurality of image processing sequences;

(g) image-processing the learning image of each of the plurality of learning sets that are more than the number of learning sets selected in the (c), of the plurality of learning sets, and that are two sets or more including the number of learning sets selected in the (c), according to the subject image processing sequence, thus generating the output image, comparing the output image and the target image associated with the learning image serving as the base of the output image, and calculating a subject evaluation value as the evaluation value;

(h) determining whether the subject image processing sequence satisfies a predetermined reference condition or not, using the subject evaluation value, wherein the method for generating the image processing sequence repeatedly executes the (b) to the (h) until the subject image processing sequence satisfies the predetermined reference condition, when selecting the number of learning sets in the (c), a probability of selection of the learning set having a predetermined value, of a plurality of subject evaluation values corresponding respectively to the two sets or more of the plurality of learning sets calculated in the (g) in a previous routine, is increased;

when the subject image processing sequence does not satisfy the predetermined reference condition, increasing a rate of selection of the learning set having the predetermined value, of the plurality of subject evaluation values corresponding respectively to the two sets or more of the plurality of learning sets, and newly selecting the learning set; and generating the sequence set that is for the newly selected learning set and that differs from the sequence set which is generated previously.

2. The method for generating the image processing sequence according to claim 1, wherein in the (b), the sequence set including the image processing sequence serving as a base of the calculation of the evaluation value satisfying an evaluation condition indicating that the degree of similarity is high, of the plurality of evaluation values calculated in the (e) in the previous routine, and an image processing sequence that is different from the image processing sequence forming the sequence set of the previous routine, is generated.

3. The method for generating the image processing sequence according to claim 1, wherein in the (g), all of learning images of the plurality of learning sets prepared in the (a) are image-processed to output the output image, and the subject evaluation value is calculated for all of the learning images.

4. The method for generating the image processing sequence according to claim 1, wherein in the (h), a statistic of the plurality of subject evaluation values corresponding to the plurality of learning sets is calculated, and when the degree of similarity indicated by the statistic is equal to or higher than a predetermined threshold, it is determined that the predetermined reference condition is satisfied.

5. The method for generating the image processing sequence according to claim 1, wherein when selecting the number of learning sets in the (c), the probability of selection of the learning set is made higher as the degree of similarity indicated by each of the plurality of subject evaluation values corresponding to the two sets or more of the plurality of learning sets, calculated in the (g) in the previous routine, becomes lower.

6. The method for generating the image processing sequence according to claim 1, wherein in the (b), each of the plurality of image processing sequences is represented by an individual formed by sequencing a plurality of genes corresponding to the image input layer and an image processing layer of the plurality of image processing layers respectively, and a gene table prescribing a coupling relationship between the sequence elements.

7. A generation device for an image processing sequence, the generation device comprising:

a processor configured to:

generate a sequence set formed of a plurality of image processing sequences, the image processing sequence of the plurality of image processing sequences representing a combination of (i) an image input layer to input an image, (ii) at least one of a plurality of image processing layers, and (iii) an image output layer to output the image after image processing, as sequence elements, the combination varying between the plurality of image processing sequences;

select, from among a plurality of learning sets where a learning set of the plurality of learning sets is a combination of a learning image prepared in advance and a target image, a number of learning sets that is smaller than the plurality of learning sets;

image-process the learning image in the selected number of learning sets-set-selected by the selection-unit, according to each of the plurality of image processing sequences;

generate an output image that is an image after the image processing for each of the plurality of image processing sequences;

compare the output image and the target image forming the selected number of learning sets with the learning image serving as a base of the output image;

calculate an evaluation value of a plurality of evaluation values indicating a degree of similarity between the output image and the target image, for each of the plurality of image processing sequences; and specify a subject image processing sequence that is the image processing sequence where the degree of similarity is highest, of the plurality of evaluation values corresponding respectively to the plurality of image processing sequences, wherein the processor image-processes the learning image of each of the plurality of learning sets that are more than the selected number of learning sets, of the plurality of learning sets, and that are two sets or more including the selected number of learning sets, according to the subject image processing sequence, and thus generates a subject output image as the output image, the processor compares the subject output image and the target image associated with the learning image serving as the base of the subject output image, and calculates a subject evaluation value as the evaluation value, the processor determines whether the subject image processing sequence satisfies a predetermined reference condition or not, using the subject evaluation value, and when the subject image processing sequence does not satisfy the predetermined reference condition, the processor increases a rate of selection of the learning set having a predetermined value, of a plurality of subject evaluation values corresponding respectively to the two sets or more of the plurality of learning sets, and newly selects the learning set, and the processor generates the sequence set that is for the newly selected learning set and that differs from the sequence set which is generated previously.

8. A non-transitory computer-readable storage medium storing a computer program, the computer program causing a computer to execute:

(a) a sequence generation function of generating a sequence set formed of a plurality of image processing sequences, an image processing sequence of the plurality of image processing sequences representing a combination of (i) an image input layer to input an image, (ii) at least one of a plurality of image processing layers, and (iii) an image output layer to output the image after image processing, as sequence elements, the combination varying between the plurality of image processing sequences;

(b) a function of selecting, from among a plurality of learning sets where a learning set of the plurality of learning sets is a combination of a learning image prepared in advance and a target image associated with the learning image, a number of learning sets that is smaller than the plurality of learning sets;

(c) a function of image-processing the learning image in the selected number of learning sets selected by the function (b), according to each of the plurality of image processing sequences, and generating an output image that is an image after the image processing for each of the plurality of image processing sequences;

(d) a function of comparing the output image and the target image associated with the learning image serving as a base of the output image, and calculating an evaluation value of a plurality of evaluation values indicating a degree of similarity between the output image and the target image, for each of the plurality of image processing sequences;

(e) a function of specifying a subject image processing sequence that is the image processing sequence where the degree of similarity is highest, of the plurality of evaluation values corresponding respectively to the plurality of image processing sequences;

(f) a function of image-processing the learning image of each of the plurality of learning sets that are more than the number of learning sets selected by the function (b), of the plurality of learning sets, and that are two sets or more including the number of learning sets selected by the function (b), according to the subject image processing sequence, thus generating the output image, comparing the output image and the target image associated with the learning image serving as the base of the output image, and calculating a subject evaluation value as the evaluation value; and (g) a function of determining whether the subject image processing sequence satisfies a predetermined reference condition or not, using the subject evaluation value, wherein the computer program causes the computer to repeatedly execute the function (a) to the function (g) until the subject image processing sequence satisfies the predetermined reference condition, the function (b) has a function of increasing a probability of selection of the learning set having a predetermined value, of a plurality of subject evaluation values corresponding respectively to the two sets or more of the plurality of learning sets calculated by the function (f) in a previous routine, when selecting the number of learning sets, and when the subject image processing sequence does not satisfy the predetermined reference condition, the computer program causes the computer to increase a rate of selection of the learning set having the predetermined value, of the plurality of subject evaluation values corresponding respectively to the two sets or more of the plurality of learning sets, and newly select the learning set, and the computer program causes the computer to generate the sequence set that is for the newly selected learning set and that differs from the sequence set which is generated previously.

* * * * *